United States Patent [19]
Pollard et al.

[11] Patent Number: 5,334,844
[45] Date of Patent: Aug. 2, 1994

[54] OPTICAL ILLUMINATION AND INSPECTION SYSTEM FOR WAFER AND SOLAR CELL DEFECTS

[75] Inventors: Howard E. Pollard, Saratoga; Robert E. Neff, Fremont; Cheryl J. Ajluni, San Jose, all of Calif.

[73] Assignee: Space Systems/Loral, Inc., Palo Alto, Calif.

[21] Appl. No.: 42,890

[22] Filed: Apr. 5, 1993

[51] Int. Cl.⁵ .............................. G01N 21/47
[52] U.S. Cl. ....................................... 250/330
[58] Field of Search ............................. 250/330

[56] References Cited

U.S. PATENT DOCUMENTS

| | | | |
|---|---|---|---|
| 4,026,656 | 5/1977 | Kusz et al. | 250/341 |
| 4,959,537 | 9/1990 | Kimoto et al. | 356/240 |
| 5,077,475 | 12/1991 | Moriya et al. | 250/330 |

*Primary Examiner*—Carolyn E. Fields
*Attorney, Agent, or Firm*—Perman & Green

[57] ABSTRACT

An optical inspection system for detecting cracks in a crystalline substrate. The crystalline substrate that is to be inspected is located in a test plane in the field of view of a video camera. A first collimated light source projects light which is passed through a long pass filter. The filtered collimated light is projected onto the reflective surface of a panel that contains surface irregularities in the same order as the wavelength of the filtered, collimated light. The light is diffused by the panel surface and reflected onto the crystalline substrate at a plurality of various angles. The light passes through the crystalline substrate and is reflected into the path of the field of view of the video camera and forms an object image from which a real image is created and may be viewed on a control monitor. Cracks in the solar cell silicon layer or glass covers can be observed on the control monitor, and printed by a video graphics printer or stored via a VCR for permanent documentation purposes.

3 Claims, 2 Drawing Sheets

OPTICAL ILLUMINATION AND INSPECTION SYSTEM FOR WAFER AND SOLAR CELL DEFECTS

BACKGROUND OF THE INVENTION

The present invention relates to optical systems for inspecting multi-layer silicon devices, and more particularly to an optical system employing near infrared illumination to detect defects in silicon layers.

Inspection systems are available in the art for detecting defects such as cracks in silicon layers, particularly in silicon layers or wafers employed in solar cells. Such systems include a source of linearly polarized infrared illumination which is directed entirely onto the solar cell device at a first selected angle. The linearly polarized infrared illumination is reflected from the silicon layer of the solar cell and an infrared video camera is positioned at a second selected angle with respect to the solar cell. The video camera, which includes an infrared linear polarization analyzer, provides a visual image of the silicon layer and cracks in the silicon wafer surface can be observed.

A typical infrared solar cell inspection system is described in the publication by J.R. Hodor, H.J. Decker, Jr., J. Barney, "Infrared Technology Comes to State-of-the-Art Solar Array Production" SPIE Vol. 819, Infrared Technology XIII (1987), pp. 22–29.

The systems previously known in the art employ infrared illumination in the 5 to 15 micron range, and also aim the collimated, linearly polarized infrared illumination directly onto the solar cell. Such systems result in an image on the video camera screen in which cracks in the silicon layer can be observed.

Available inspection methods, known in the art are extremely complex in design and use, and hindered by large weight constraints. All of the various systems known or proposed to date may no longer be considered practical since the complexity, size and weight constraints of the systems make them too expensive and not portable enough for use in a dynamic aerospace manufacturing and test environment.

SUMMARY OF THE INVENTION

An object of the present invention is to provide an optical inspection system for observing cracks in silicon substrates, but may also be used to detect cracks in gallium arsenide (GaAs) or germanium (Ge) substrates, which requires fewer components than prior art systems.

Another object of the present invention is to provide an optical inspection system for silicon wafer defects which clearly distinguishes between cover layer cracks and cracks in the silicon wafer.

A further object of the present invention is to provide an optical inspection system for silicon wafers in solar array panels that gives consistent results for a number of inspections with minimum risk to the solar panels.

In accordance with the present invention therefore, an optical inspection system for solar cells and the like is disclosed wherein the illumination employed is in the near infrared frequencies, and wherein the illumination is diffused and directed onto the solar cell being inspected at a plurality of separate angles.

DESCRIPTION OF A PREFERRED EMBODIMENT OF THE INVENTION

Figure 1:
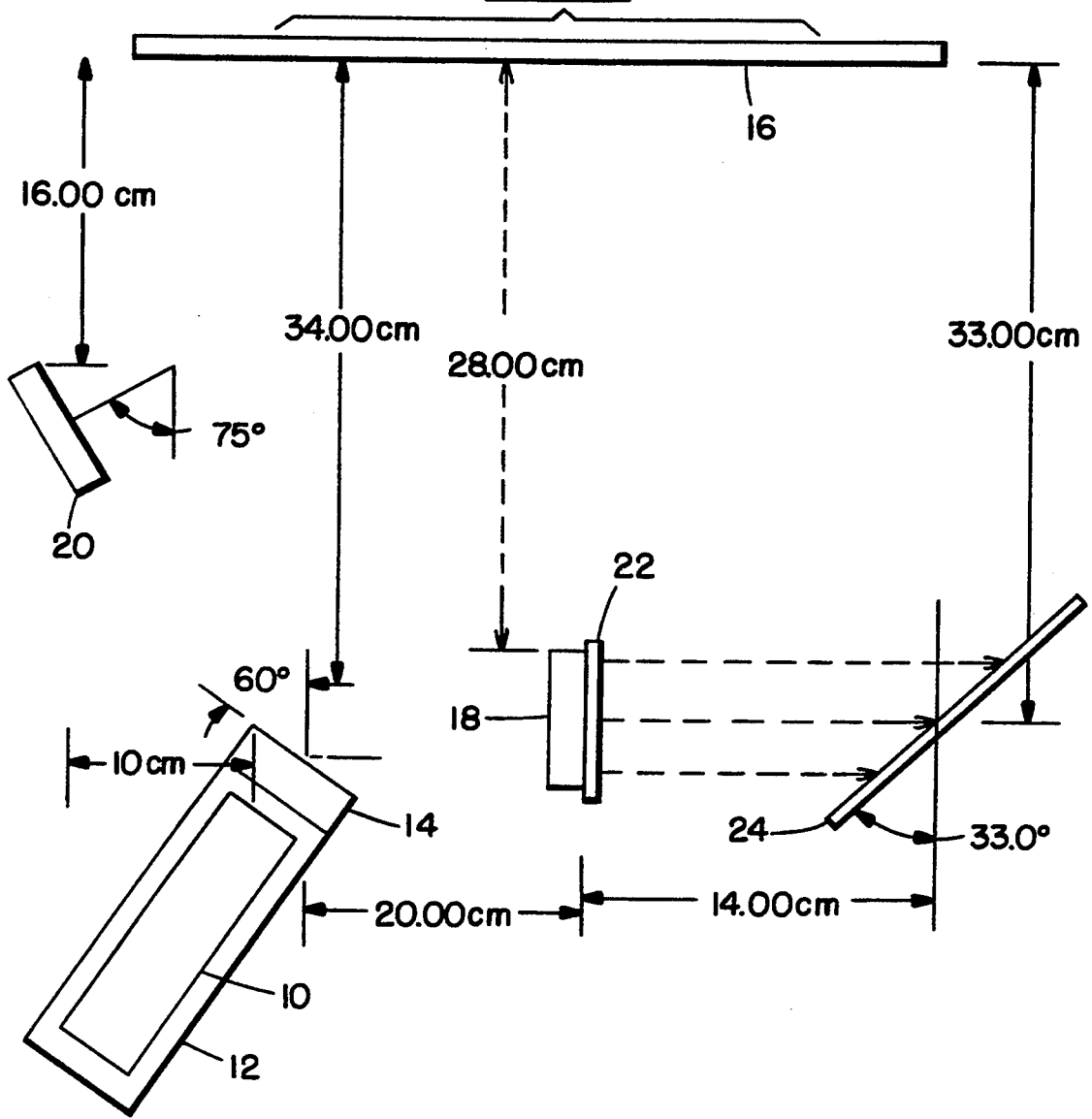
FIG. 1 is a schematic block diagram of the components of an optical inspection system according to the principles of the present invention.

Referring to FIG. 1 an embodiment of an optical inspection system for detecting cracks in a silicon wafer or in intermediate layers of a solar cell is illustrated including a laser 10 for providing a beam of collimated illumination. Laser 10 may be a typical HeNe laser available in the art. A video camera 12 is disposed co-linear with laser 10 and includes a macro-zoom lens 14. The laser 10 is used as a guide for sighting video camera 12 at a selected target location. Camera 12 is sensitive to near infrared frequencies and is also available in the art. The solar panel 16 that is to be inspected is located in a test plane in the path of the illumination from laser 10 and in the field of view of video camera 12.

A first collimated light source 18, for example a quartz halogen lamp, provides illumination 0.9 to 1.2 micron near infrared spectrum is projected through and filtered by a long pass filter 22 which passes wavelengths of 1.0 micron. The filtered collimated light from light source 18 is projected onto the surface of white paper panel 24. The solar panel 16 may also be illuminated by uncollimated unfiltered near infrared light directed at an angle from a second quartz-halogen light source 20. FIG. 1 includes typical dimensions for the placement of the described system components. These dimensions are not critical and are included to show the compactness of the system of the present invention.

The surface of the white paper 24 contains irregularities on the order of 1.0 micron which is also on the same order as the wavelength of the near infrared illumination which passes through filter 22. These irregularities cause the light reflected from the surface of white paper 24 to diffuse. The white paper 24 is positioned such that the diffuse light reflected therefrom falls upon the surface of the solar panel 16 positioned in a test plane. Because the light rays reflected from white paper 24 are diffuse they strike the surface of the solar panel 16 at a plurality of various angles.

Figure 2:
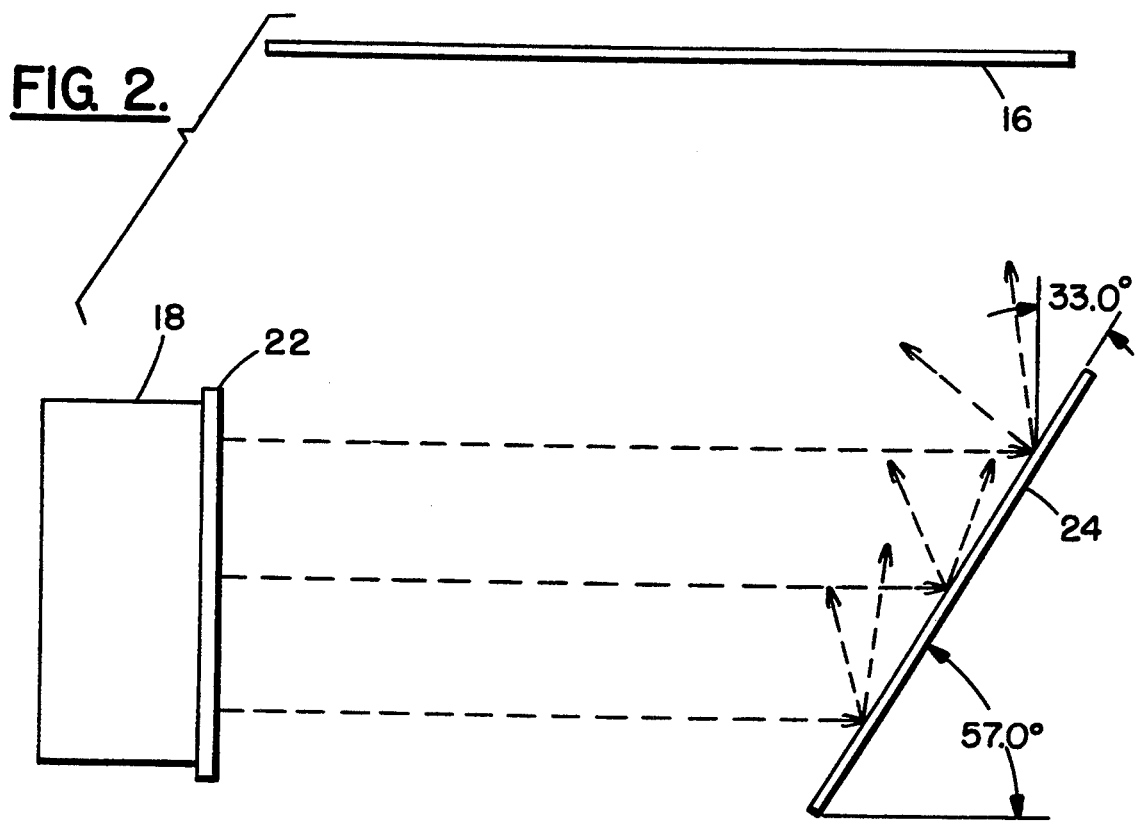
FIG. 2 is a schematic illustration showing typical optical paths for the light sources used in the system of FIG. 1.

Referring to FIG. 2, an illustration is provided showing the light rays from lamp 18 and filter 22 reflected off white paper 24 at various angles toward solar panel 16 because of the diffuse reflection from the white paper 24 surface.

Figure 3:
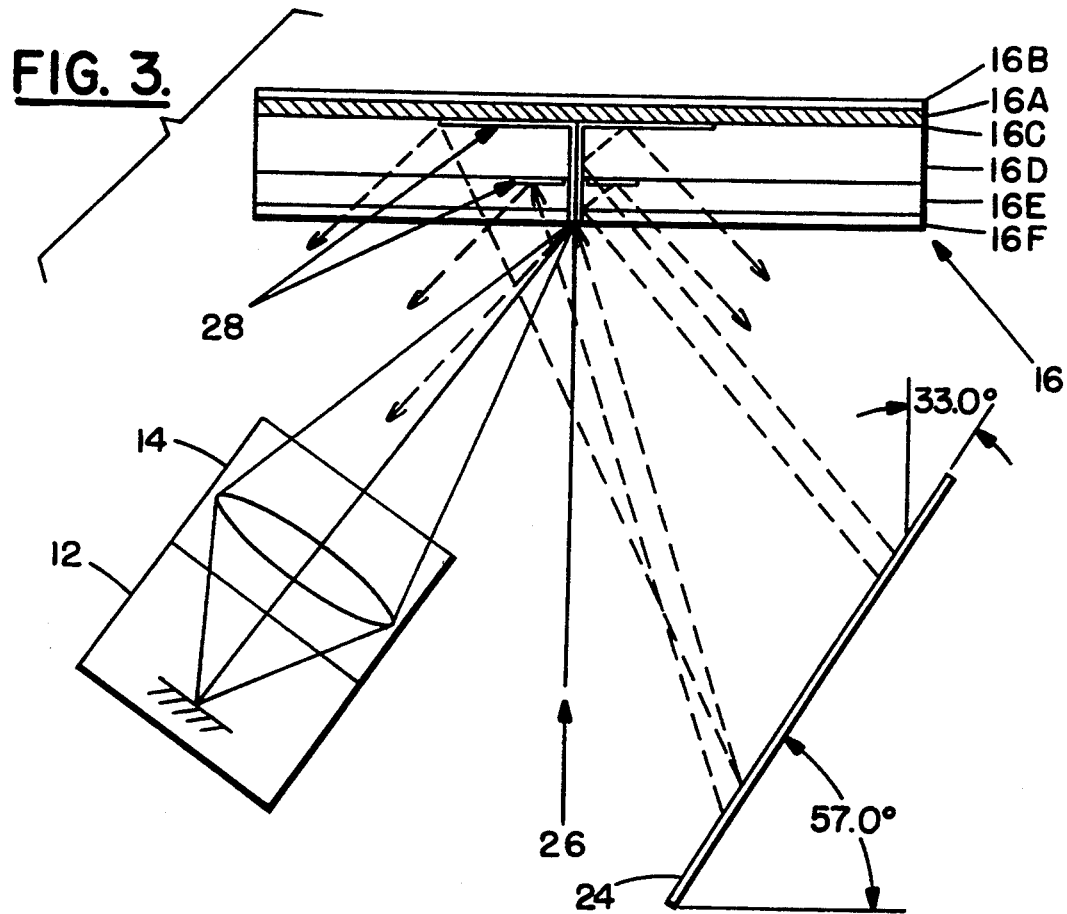
FIG. 3 is a schematic illustration showing the interaction of the light rays of the system of FIG. 1 at the various interfaces of a typical solar cell.

Referring to FIG. 3, an illustration is provided showing the component layers of a solar cell of panel 16 which include the solar cell material 16A having a metallized back surface 16B, which supports a layer 16A of silicon germanium or a GaAs material. A layer of coverglass 16D is disposed on solar cell 16A by cell adhesive 16C and a coverglass 16E with an anti-reflective coating 16F is located on coverglass 16D. The structure 16A, 16B, 16C, 16D, 16E, and 16F in FIG. 3 depicts one solar cell of the solar panel 16. Since light bends at the interface between two transparent substances with different indices of refraction, each near infrared light ray reflected from the diffuse surface of white paper 24 will strike the coverglass layer 16E and be partially transmitted through the glass at various angles according to Snell's Law For Refraction (M1 sin $\phi_1$=M2 sin $\phi_2$ where M$_1$ is the index of refraction for the first transparent substance.

M$_2$ is the index of refraction for the second transparent substance.

$\phi_1$ is the angle of the light ray with respect to the interface as it enters from the first substance.

$\phi_2$ is the angle of the light ray with respect to the interface as it exits into the second substance.

The near infrared light reflected from the white paper 24 will also strike the coverglass 16E and be partially reflected according to the Law of Reflection which states that the incident angle $\phi_i$ is equal to the angle of reflection $\phi_i$ (o$_i$=$\phi_r$).

Thus, each individual ray of light reflected from the white paper 24 and falling on coverglass 16E will consist of two subsequent rays; a transmitted (refracted) ray and a reflected ray. While both reflection and refraction of the light rays will occur at the interface between the coverglass 16D and the adhesive 16C, no total internal reflections will occur because the light rays are travelling into a more optically dense substance.

All of the light rays have four transitions, or angle changes, they must undergo as they pass through, or are reflected from, the other various interfaces within the layers of the solar cell. Initially each light ray must cross the interface between the anti-reflective coating 16F and the coverglass 16E, the interface between the coverglass 16D and the adhesive 16C, the interface between the adhesive 16C and the silicon wafer 16A, and lastly the interface between the silicon 16A and the metallized back surface 16B. All interfaces allow for the light rays to either be reflected or transmitted through to the next media. Total internal reflection will only occur for certain light rays at the interface between air and the anti-reflective coating 16F. As the light rays pass through the solar cell interfaces some will be reflected back toward the white paper 24, while others, as shown in FIG. 3, will be reflected in the direction of the field of view of the camera 12 and its zoom lens 14. Those rays which fall in the path of the field of view of the Camera 12, become the object image from which a real image is created and may be viewed on a control monitor (not shown) which is associated with the video camera 10. One skilled in the art will appreciate that camera 12 may also include provision for video tape recording, and a video graphics printer for permanent documentation of the defect.

The image which is seen on the control monitor arises solely from the contribution of the first collimated quartz-halogen light source 18 with its attached long pass filter 22. The second light source 20, an unfiltered uncollimated quartz-halogen light is only used to illuminate the solar panel 16 when it is necessary to verify whether a detected crack is a crack in the coverglass or a crack in the bare silicon of the cell. All interfaces of the layers of the solar cell will result in shadows appearing on the surface of the silicon layer 16A, but the only two surfaces of concern are those of the coverglass and bare solar cell.

In FIG. 3, the dark line within the solar cell perpendicular to the surface 16A designated by reference number 26 indicates a crack in the bare silicon and reference number 28 indicates shadows of the actual crack 26 created by illuminating the cracks 26 at the various interfaces.

Figure 4:
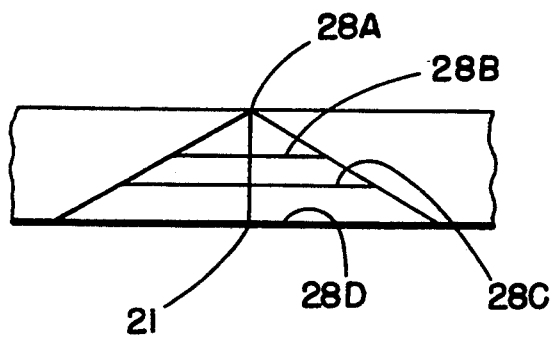
FIG. 4 is a more detailed illustration of the solar cell interfaces and the shadows produced by cracks therein.

FIG. 4 is an illustration of the various shadows which are created in the layers of the solar cell at the separate interfaces. Shadow 28A is at the anti-reflective coating/coverglass interface, shadow 28B is at the coverglass/adhesive interface, shadow 28C is at the adhesive/silicon interface and shadow 28D is at the silicon, metallization interface.

The near infrared light which is used to detect bare solar cell cracks and coverglass cracks comes originally from the light source 18. Both coverglass cracks and solar cell cracks may be viewed simultaneously at the camera. That is to say from the view of the camera they appear to be superimposed on top of one another, when in reality they are on two different planes. To a trained observer looking at a control monitor screen with a picture of a cracked solar cell it would be simple to tell the difference between a coverglass crack or a solar cell crack. Coverglass tends to shatter or crack in a curved manner, similar to the strands of a spider web. Bare solar cell will crack in 45° or 30° straight lines depending on the crystal orientation of the bare solar cell material. To an untrained eye it might not be so easy to make the clarification. Viewing is more difficult if the coverglass breaks over the cell so that you have both surfaces cracked but with your eye you can not be sure if both surfaces are cracked or if it is really just one surface. This is why the secondary light source 20 is used; as a way to support the determination. If the light source 20 is turned on and you see a series of bright dots reflected back at you on the control monitor then you know the coverglass is definitely cracked. More particularly, the secondary light source 20 is turned on to verify whether or not there is any total internal reflection of the light rays. If in fact the light beams from the secondary source 20 exhibit the characteristic of total internal reflection then it determines that the coverglass is effectively cracked. This phenomenon occurs when a single light ray strikes the crack in the glass at such an angle that is either equal to or greater than the critical angle for the interface from the air to the anti-reflective coating on the coverglass.

What has been described is a simple, compact and portable test system to easily identify and document solar cell and coverglass cracks for accurately characterizing the reliability and quality of the solar cells contained on a solar panel. The present invention offers the capability to easily verify the reliability of hardware on site before it is launched into the space environment. Its flexibility of use and implementation into any sort of test station make it not only feasible, but cost effective as well, and thus a particularly essential asset to any space oriented application.

What is claimed is:

1. An optical inspection system for observing physical defects in a crystalline substrate structure comprising:

a source of collimated light beam, means disposed in the path of said collimated light beam for filtering said collimated light beam to pass specific wavelengths of said collimated light beam, means disposed in the path of said collimated light beam for diffusing said collimated light beam at said specific wavelengths and directing the diffused light onto and illuminating said crystalline substrate structure, and observation means directed onto said crystalline substrate structure and responsive to said collimated light and said diffused light for providing an image of said crystalline substrate structure wherein physical defects in said crystalline substrate structure are apparent in said image, wherein said physical defects are cracks in said crystalline substrate structure, wherein said source of collimated light produces light in the near infrared spectrum, and wherein said diffused light directed onto said crystalline substrate structure by said diffusing means illuminates said crystalline substrate structure to produce shadows representative of said cracks which are apparent in said image of said observation means, and wherein said source of near infrared collimated light is a quartz-halogen lamp, said filtering means is a long pass filter, and said diffusing means is a structure having a reflective surface disposed in the path of the filtered collimated light for diffusing and reflecting the filtered collimated light rays onto said crystalline layer structure at a plurality of separate angles.

2. An optical inspection system according to claim 1 wherein said crystalline substrate structure is a multilayered structure including a crystalline substrate, a transparent layer bonded onto said crystalline substrate and an anti-reflective coating disposed on said transparent layer, and wherein said system further includes a source of a uncollimated light directed onto said crystalline substrate structure for producing shadows representative of cracks in said transparent layer wherein said shadows representative of said cracks in said crystalline substrate and said shadows representative of cracks in said transparent layer are apparent and distinguishable in said image of said observation means.

3. An optical inspection system according to claim 1 wherein said collimated, filtered light has a wavelength of approximately 1.0 micron and wherein said structure having a reflective surface has a surface with irregularities in the order on 1.0 micron.

* * * * *